United States Patent [19]

Mason et al.

[11] Patent Number: 4,697,583

[45] Date of Patent: Oct. 6, 1987

[54] FOUR-POINT ANTERIOR CRUCIATE LIGAMENT BRACE

[75] Inventors: Bradley R. Mason, Carlsbad; Jeffrey T. Mason, Escondido; Patrick W. Cawley, San Diego, all of Calif.

[73] Assignee: Don Joy Orthopedic, Inc., Carlsbad, Calif.

[21] Appl. No.: 696,185

[22] Filed: Jan. 29, 1985

[51] Int. Cl.⁴ ............................................... A61F 5/00
[52] U.S. Cl. ................................. 128/80 C; 128/80 F
[58] Field of Search ................. 128/80 R, 80 C, 80 F, 128/88

[56] References Cited

U.S. PATENT DOCUMENTS

| | | | |
|---|---|---|---|
| Re. 30,501 | 2/1981 | Almeida | 128/80 C |
| 2,144,641 | 1/1939 | Snyder | 128/80 C X |
| 2,179,903 | 11/1939 | Spears | 128/80 C |
| 2,467,907 | 4/1949 | Peckham | 128/80 C |
| 3,817,244 | 6/1974 | Taylor | 128/80 C |
| 3,901,223 | 8/1975 | May | 128/80 F |
| 4,088,130 | 5/1978 | Applegate | 128/80 F |
| 4,245,629 | 1/1981 | Cummins | 128/80 C |
| 4,249,524 | 2/1981 | Anderson | 128/80 C |
| 4,271,831 | 6/1981 | Deibert | 128/80 C |
| 4,320,747 | 3/1982 | Daniell, Jr. | 128/80 C |
| 4,337,764 | 7/1982 | Lerman | 128/80 F |
| 4,353,361 | 10/1982 | Foster | 128/80 C |
| 4,361,142 | 11/1982 | Lewis et al. | 128/80 C |
| 4,372,298 | 2/1983 | Lerman | 128/88 X |
| 4,381,768 | 5/1983 | Erichsen et al. | 128/80 C |
| 4,493,316 | 1/1985 | Reed et al. | 128/80 C |
| 4,503,846 | 3/1985 | Martin | 128/80 C |
| 4,506,661 | 3/1985 | Foster | 128/88 X |
| 4,520,804 | 6/1985 | DiGeorge | 128/80 C |

*Primary Examiner*—Edgar S. Burr
*Assistant Examiner*—Moshe I. Cohen
*Attorney, Agent, or Firm*—Albert L. Gabriel

[57] ABSTRACT

A knee brace for externally replacing the function of a torn anterior cruciate ligament. The brace has femur and tibia levers hinged proximal the knee joint. The femur lever has an upper high cuff which bears against the front of the thigh and a lower strap which applies anterior force to the back of the thigh proximal the knee, while the tibia lever has a lower calf cuff which bears against the back of the calf and an upper strap which applies posterior force to the front of the tibia proximal the knee. Thus, the two straps apply a differential force couple forwardly to the femur and rearwardly to the tibia proximal the knee joint which serves the anterior cruciate ligament function. A resilient tubular undersleeve anchors the brace against downward migration on the leg.

25 Claims, 11 Drawing Figures

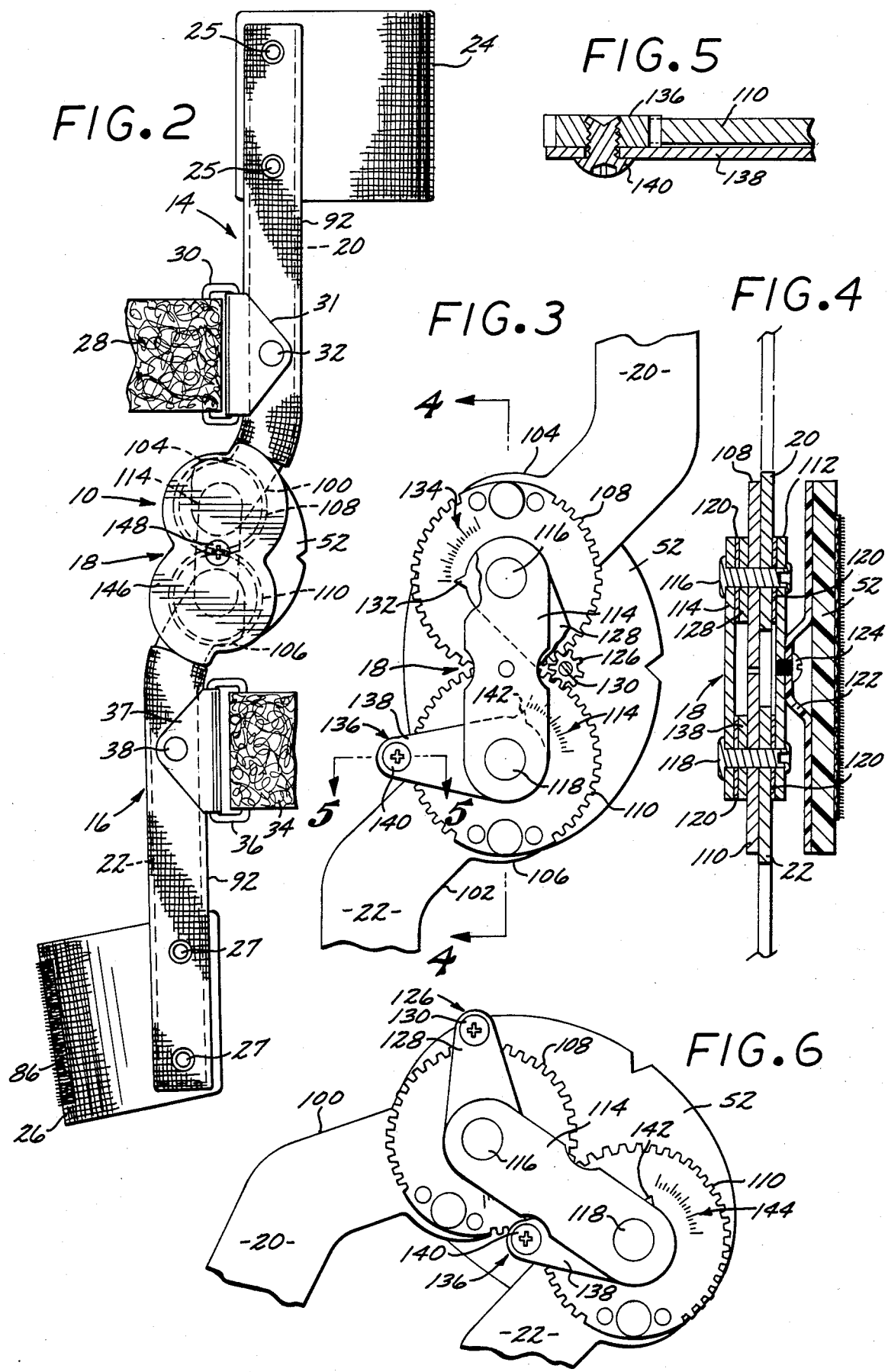

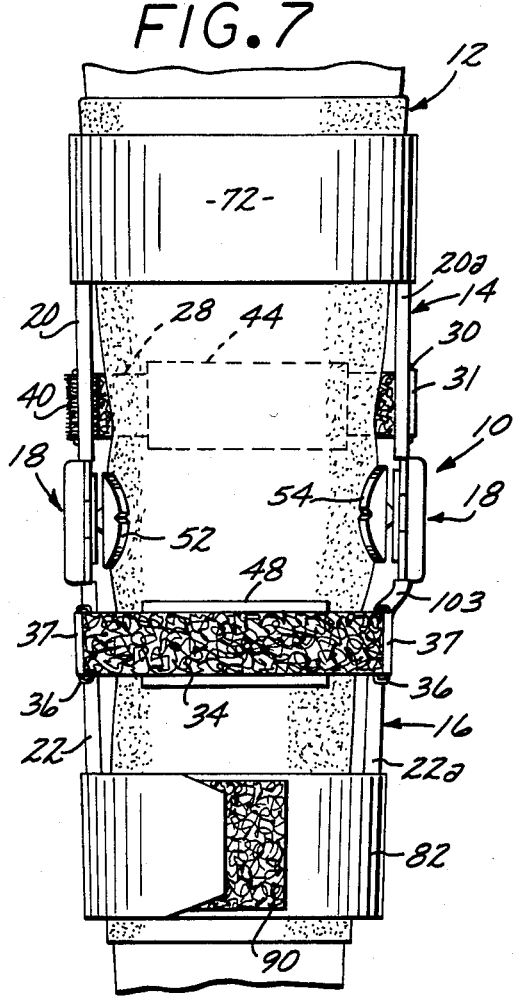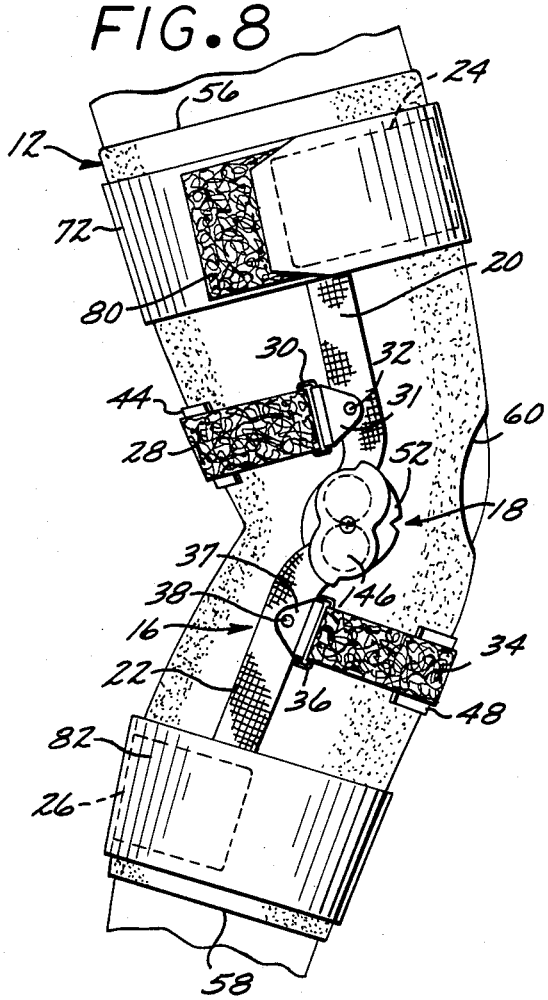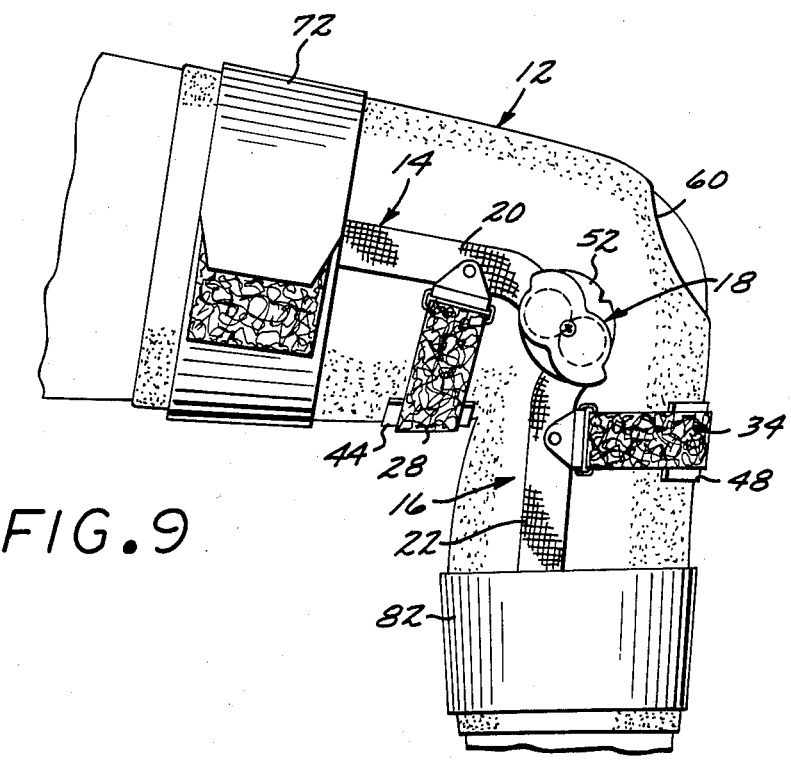

FOUR-POINT ANTERIOR CRUCIATE LIGAMENT BRACE

BACKGROUND OF THE INVENTION

1. Field of the Invention

The present invention relates to orthopedic devices for injured knees, and it relates more particularly to a knee brace adapted to serve as an external replacement or substitute for a torn anterior cruciate ligament.

2. Description of the Prior Art

The human knee is a very complex mechanism that is highly vulnerable to injury in various sports, particularly such contact sports as football, soccer and basketball. The primary front/rear locating means within the knee joint is a pair of crossed ligaments called the cruciate ligaments which connect between the femur and the tibia. These are the anterior and posterior cruciate ligaments. The anterior cruciate ligament controls forward drawer shifting or translocation of the tibia relative to the femur, while the posterior cruciate ligament controls rearward drawer shifting or translocation of the tibia relative to the femur. By far the most commonly injured of the cruciate ligaments is the anterior cruciate ligament, torn anterior cruciate ligaments being a major crippler of athletes involved in contact sports. Heretofore, an athlete having a torn anterior cruciate ligament was generally not able to continue athletic performance without corrective surgery, and even then 100 percent rehabilitation was not likely.

Applicants are not aware of anyone having heretofore specifically addressed the possibility of an external substitute or replacement for a torn anterior cruciate ligament in the form of an orthopedic device, and none of the many knee orthotics of which applicants are aware was or is capable of compensating for an anterior cruciate ligament tear sufficiently for athletic performance.

Applicants have determined that in order for a knee brace to be effective as a substitute or replacement for a torn anterior cruciate ligament, it must include a leverage system capable of applying a strong differential force anteriorly to the femur and posteriorly to the tibia proximal the knee joint, yet none of the prior art knee braces of which applicants are aware are directed to the application of such differential force, or are in any way capable of applying the leverage necessary to achieve such differential force.

One of the factors applicants have found to be desirable in achieving the necessary leverage for a satisfactory external substitute for a torn anterior cruciate ligament is the use in the substitute brace of hinges on both the lateral and medial sides of the knee that are both bicentric and geared. Examples of such bicentric, geared hinges in knee orthotics are found in U.S. Pat. No. 4,381,768 to Erichsen, and U.S. Pat. No. 4,372,298 to Lerman. Other examples are seen in two prior U.S. patent applications in which applicants are joint inventors, Ser. No. 474,004, filed Mar. 10, 1983 for Articulating Graphite Knee Stabilizer, and Ser. No. 657,356, filed Oct. 3, 1984 for Athletic Knee Protector. Applicants said Application Ser. No. 474,004 disclosed pinion stops associated with the hinge gears for limiting the extent of flexion and extension. Another form of polycentric hinge that was not geared but had a similar action was disclosed in Cummins U.S. Pat. No. 4,245,629. Despite the presence of such bicentric hinges with geared or gear-like connections in these prior knee orthotics, none of them had a structural arrangement capable of applying leverage which would produce a force couple on the femur and tibia proximal the knee joint such as would simulate the force of a healthy anterior cruciate ligament.

Applicants are aware of another group of prior art knee orthotics having polycentric hinges that did not have geared or gear-like connections, and that also were incapable of applying leverage which could produce the necessary differential force to serve the function of an anterior cruciate ligament. These devices are disclosed in U.S. Pat. Nos. 2,467,907 to Peckham, 3,901,223 to May, Reissue 30,501 to Almeida, 4,249,524 to Anderson, and 4,271,831 to Deibert.

Applicants are also aware of a number of knee brace-type devices which utilize only single-pivot hinges, and like the other devices referred to above, none of these are capable of applying leverage that would produce a force couple corresponding in effect to the anterior cruciate ligament. Such devices are shown in U.S. Pat. Nos. 2,144,641 Snyder, 3,817,244 Taylor, 4,088,130 Applegate, 4,320,747 Daniell, Jr., and 4,353,361 Foster.

The basic purpose of all of this large number of prior art knee brace-type devices is simply to increase the stability of an injured knee, and for the most part such devices have simply constituted supplemental hinge structures strapped to the thigh and calf, intended to give added mechanical pivot strength to the knee.

Most of these prior art devices involve straps that completely and tightly encircle the leg above and below the knee in such a way that any force that may incidentally be applied in a direction to aid the anterior cruciate ligament would be generally cancelled by an opposite force. Such leg-encircling straps, to have any substantial effect in increasing the general stability of the knee, must generally be tightened to the point where they are likely to interfere with blood circulation.

In addition to their general function of stabilizing the knee, the leg-encircling straps characteristically used in prior art knee braces helped to resist the tendency of all such devices to migrate downwardly along the leg in use, both from the effects of gravity and because of the general tapering of the leg. Nevertheless, even with full leg-encircling straps, such prior art devices all had a general tendency to migrate downwardly along the leg, particularly if they were used during the rigors of athletic performance.

SUMMARY OF THE INVENTION

In view of these and other problems in the art, it is a general object of the present invention to provide a knee brace which serves as an external replacement or substitute for a torn anterior cruciate ligament.

Another object of the invention is to provide a knee brace which embodies a novel four-point leverage system that applies a force couple anteriorly to the femur and posteriorly to the tibia proximal the knee joint so as to accomplish the same function as an anterior cruciate ligament which may be disabled.

Another object of the invention is to provide an anterior cruciate ligament knee brace wherein a posterior thigh strap applies anterior force to the femur proximal the knee joint without opposition from any strap or other structure engaged around the front of the thigh, and an anterior tibial strap applies posterior force proximal the knee joint without opposition from any strap or other structure engaged around the back of the calf.

A further object of the invention is to provide an anterior cruciate ligament brace having a femur lever and a tibia lever which are joined at both the lateral and medial sides of the knee joint by bicentric, geared hinges that have hinging movements simulating those of the knee joint yet positively resist front/rear relaxation or tilting at the hinges for positive application by the levers of forces to the femur and tibia serving the function of a replacement anterior cruciate ligament.

A further object of the invention is to provide a four-point anterior cruciate ligament brace of the character described having a femur lever and a tibia lever, wherein the fulcrum of the femur lever is an open, arcuate anterior thigh cuff and the fulcrum of the tibia lever is an open, posterior calf cuff, and anterior cruciate ligament-simulating leverage is applied to the knee joint by an open, arcuate adjustable posterior thigh strap urging the femur anteriorly and an open, arcuate, adjustable anterior tibial strap urging the tibia posteriorly.

Yet a further object of the invention is to provide an anterior cruciate ligament brace of the character described wherein the posterior thigh strap and anterior tibial strap which apply the anterior cruciate ligament-type force to the knee joint are enabled to each have approximately 180° of engagement with the respective limbs by having femoral and tibial side bars of the brace displaced forwardly and rearwardly, respectively, along the sides of the leg.

Another object of the invention is to provide a resilient tubular undersleeve for a knee brace that is at least substantially coextensive in length with the brace and to which the brace is releaseably attachable, as by Velcro means, to prevent downward migration of the brace along the leg, such tubular undersleeve having particular utility in combination with the four-point anterior cruciate ligament brace of the invention wherein the four points of force are applied by open cuffs and straps that do not extend all of the way around the leg.

The knee brace of the present invention consists essentially of a pair of levers, a femur lever and a tibia lever, hinged together proximal the knee. Each of the two levers consists of a pair of side bars hinged to the side bars of the other lever and joined together by a fulcrum cuff at the ends remote from the hinge, the femur lever having an anterior thigh cuff which bears against the front of the thigh, and the tibia lever having a posterior calf cuff which bears against the rear of the calf. The femur lever also includes an adjustable posterior thigh strap looped from one side bar to the other around the back of the thigh and tightened to apply anterior force to the femur proximal the knee joint. The tibia lever has a complementary adjustable anterior pretibial strap looped from one side bar to the other around the front of the shin and tightened to apply posterior force to the tibia proximal the knee joint.

The hinge structure between the femur and tibia levers is preferably a bicentric, geared hinge on each side of the brace connecting the femoral and tibial side bars on the respective sides, the gears on each side being rigidly connected to the respective femoral and tibial side bars so as to prevent any possible relaxation between the hinged side bar ends at the hinge joint, and thereby prevent any possible relaxation of the posterior thigh strap and anterior tibial strap which are applying a differential force forwardly on the femur and rearwardly on the tibia to perform the same function as the anterior cruciate ligament in the knee. As the knee bends from an extended position toward a flexed position, the hinge gears attached to the tibial side bars climb or roll rearwardly along the hinged gears attached to the femoral side bars, thereby increasing the amount of traction of the anterior tibial strap on the tibia, and hence the effectiveness of the force functioning as an anterior cruciate ligament force.

The hinged ends of the femoral side bars angle posteriorly, while the hinged ends of the tibial side bars angle anteriorly, providing a substantial anterior offset of the main lengths of the femoral side bars from the hinges and a substantial posterior offset of the main lengths of the tibial side bars from the hinges, thereby enabling each of the posterior thigh strap and anterior tibial strap to have at least approximately 180° of strap loop arc to assure maximum mechanical advantage for each of the femur and tibia levers.

A thin elastomeric undersleeve, preferably of foam Neoprene, is slipped over the leg prior to attachment of the brace to the leg, this undersleeve having a longitudinal extent somewhat greater than the brace itself to assure longitudinal registry of the brace over the undersleeve. The brace is interlocked with the undersleeve at three longitudinal locations, the anterior thigh cuff, the posterior calf cuff, and proximal the knee joint at a pair of condyle pads mounted on the hinge structures. A patellar relief aperture is provided in the undersleeve. The undersleeve prevents downward migration of the brace, and also improves patient comfort while wearing the brace. Longitudinal stability of the brace on the leg may be further improved by encircling the leg with elastic overwrap straps in the regions of the thigh and calf cuffs. The elastic overwrap straps also secure the open-cuffed ends of the brace to the thigh and calf so that hinge stops in the brace are enabled to function as positive blocks against hyperextension of the joint.

As described in detail hereinafter in the Detailed Description, clinical tests by applicants have established that the present invention is completely effective in externally replacing or substituting for a torn anterior cruciate ligament, and that on the average the present invention is even capable of controlling tibial anterior drawer movement relative to the femur in the injured knee of a patient better than the real anterior cruciate ligament controls it in the good knee.

BRIEF DESCRIPTION OF THE DRAWINGS

These and other objects of the invention will become more apparent in view of the following description taken in conjunction with the drawings, wherein:

FIG. 2 is a side elevational view of the brace, looking from the lateral side, with portions of the posterior thigh strap and anterior tibial strap removed, the brace being shown in an extended condition;

FIG. 3 is an enlarged, fragmentary side elevational view, wtih portions broken away, illustrating the preferred bicentric, geared hinge construction employed in the brace, with the brace in an extended condition;

FIG. 4 is a fragmentary vertical section taken on the line 4—4 in FIG. 3;

FIG. 5 is a further enlarged, fragmentary horizontal section taken on the line 5—5 in FIG. 3;

FIG. 6 is a fragmentary side elevational view similar to FIG. 3, but with the brace in a flexed condition;

FIG. 7 is a front elevational view of the brace of the invention mounted over the tubular undersleeve of the invention on a leg, the brace being in an extended condition;

FIG. 8 is a side elevational view similar to FIG. 7, showing the lateral side of the brace in a partially flexed condition;

FIG. 9 is a view similar to FIG. 8, showing the brace in a more flexed condition.

DETAILED DESCRIPTION

Figure 1A:
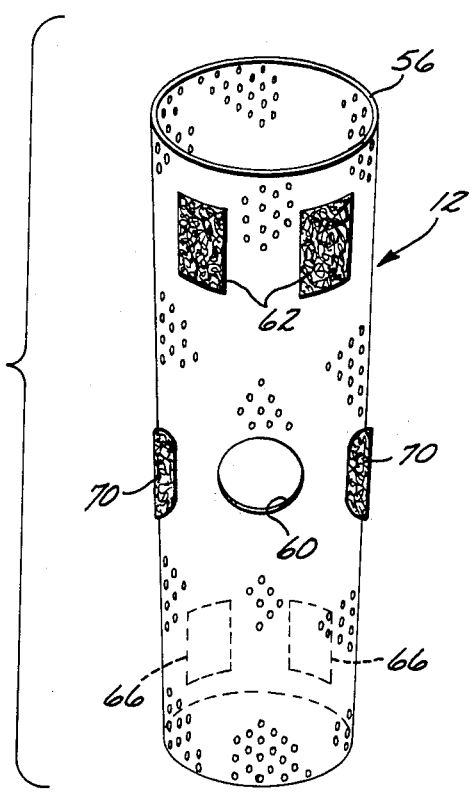
FIG. 1A is a perspective view showing the tublar sleeve utilized with the instant knee brace.

Referring to the drawings, and at first particularly to FIGS. 1, 2, and 7–10 thereof, a brace according to the invention which provides an external replacement or substitute for the anterior cruciate ligament is generally designated 10. The particular brace 10 illustrated in the drawings is adapted to serve the function of the anterior cruciate ligament of a right leg, and a brace according to the invention for the left leg will have its parts reversed or arranged as a mirror image relative to those of the brace 10 shown in the drawings when viewed from the front or rear. The braces of the invention for the right and left legs will appear the same when viewed from either the lateral side or the medial side.

Figure 1B:
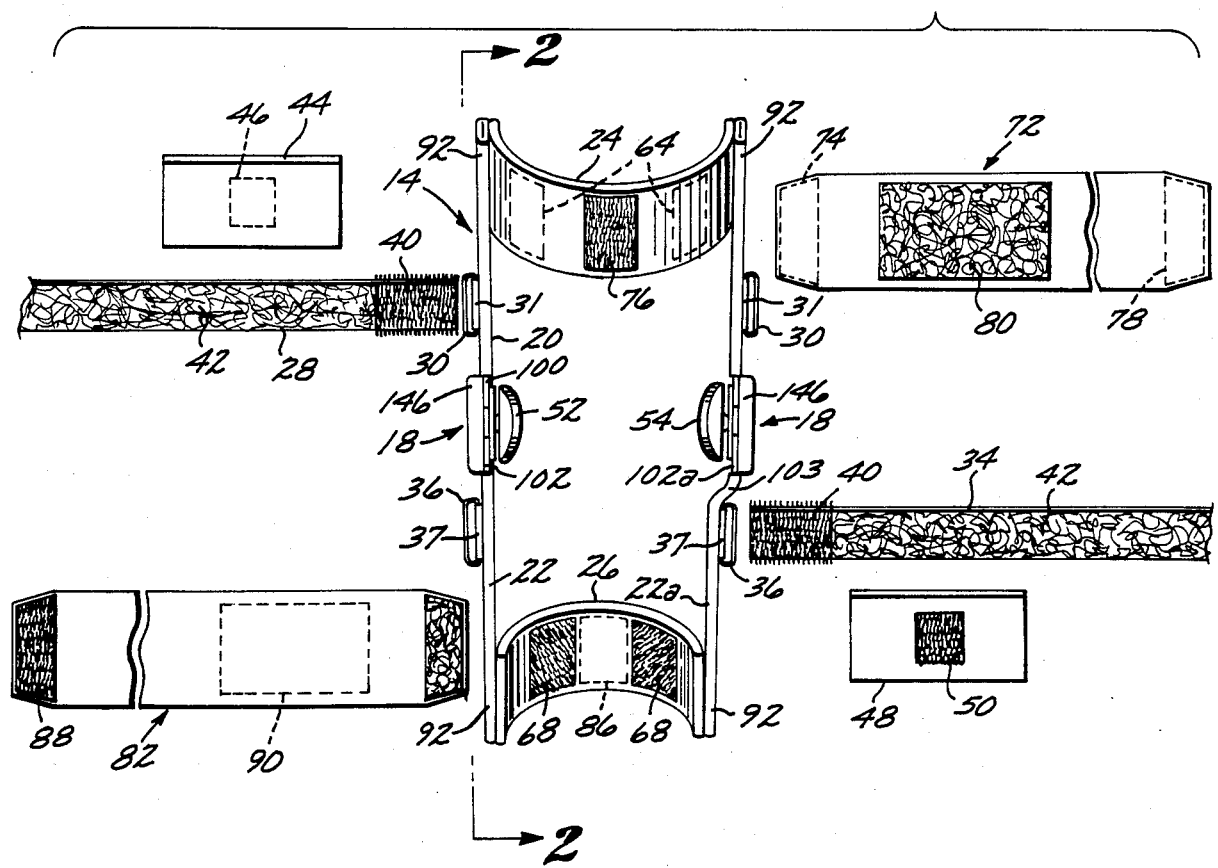
FIG. 1B is an exploded perspective view showing the knee brace looking generally from the front thereof.

FIG. 1 shows all of the components of the brace 10 of the invention layed out as viewed from the front, with the various separable straps, pads, overwraps, and the tubular undersleeve, separated from the hinge brace structure per se to facilitate understanding of the construction of the individual separable parts and how they are assembled to form the operative composite four-point anterior cruciate ligament brace 10. The brace 10 per se will be considered in the following description to consist of the hinged mechanical brace structure with its directly associated straps, pads, and overwraps, while the tubular undersleeve separately shown in FIG. 1 is generally designated 12, the undersleeve 12 being slideably engaged over the knee and large portions of the thigh and calf as shown in FIGS. 7–10 prior to attachment of the brace 10 to the leg.

The brace 10 is best considered as generally consisting of a pair of levers connected by means of a hinge structure. Thus, the brace 10 includes an upper femur lever generally designated 14 and a lower tibia lever generally designated 16, the levers 14 and 16 being operatively connected at the lateral and medial sides of the leg proximate the knee by means of a pair of hinges each of which is designated 18.

The femur lever 14 includes a pair of generally parallel, elongated, flat side bars which extend generally longitudinally along opposite sides of the thigh, these being a lateral or outer femoral side bar 20 and a medial or inner femoral side bar 20a. Similarly, the tibia lever 16 includes a pair of elongated, generally parallel but slightly downwardly converging, flat tibial side bars adapted for location generally longitudinally along opposite sides of the calf, these being lateral or outer tibial side bar 22 and medial or inner tibial side bar 22a. The femoral side bars 20 and 20a are rigidly connected proximate their upper ends to opposite posterior ends of an anterior thigh cuff 24 as by means of rivets 25 shown in FIG. 2, the anterior thigh cuff 24 extending arcuately anteriorly from the upper ends of the femoral side bars 20 and 20a. Anterior thigh cuff 24 serves as the fulcrum of the femur lever 14. Tibial side bars 22 and 22a are similarly rigidly connected proximate their lower ends to the anterior ends of a posterior calf cuff 26 as by means of rivets 27 as shown in FIG. 2, the posterior calf cuff 26 extending arcuately rearwardly from the lower ends of tibial side bars 22 and 22a. The posterior calf cuff 26 serves as the fulcrum of the tibia lever 16.

The anterior thigh cuff is preferably made substantially rigid, but formably adjustable to accommodate various thigh curvatures. Applicants have found it desirable to produce the brace 10 of the invention in four sizes to accommodate all sizes of patients, and generally one arcuate curvature of the anterior thigh cuff 24 for each size brace 10 will fit most thighs of the wearers because the thigh curvatures of such wearers do not generally vary appreciably. The anterior thigh cuff 24 may have a generally rigid but formably adjustable sheet metal core, preferably of aluminum, laminated on both sides with a padding material such as foam Neoprene, making the anterior thigh cuff 24 a thick, generally rigid structure.

The posterior calf cuff 26 is a thick structure made with a flexible but nonstretchable core of a plastic material such as polyethylene, also laminated on both sides with a padding material such as foam Neoprene. Calf cuff 26 is made flexible so as to accommodate the wide variety of calf girths found in patients for each of four sizes of braces 10, and to allow adjustment of the tibial side bars 22 and 22a against twisting relative to hinges 18 which might otherwise be caused by undersized or oversized calves.

The element of femur lever 14 adapted to apply anterior force to the femur proximal the knee joint is an adjustable posterior thigh strap 28 looped around the back of the thigh between a pair of elongated eyelets 30 connected to side bars 20 and 20a by respective eyelet holders 30 and pivot pin rivets 32. Conversely, the force-producing element of tibia lever 16 add to apply posterior force to the tibia proximal the knee joint is anterior pretibial strap 34, which is looped over the front of the shin between a pair of elongated eyelets 36 attached to the respective tibial side bars 22 and 22a by means of respective eyelet holders 37 and pivot pin rivets 38. The posterior thigh strap 28 and anterior pretibial strap 34 are both nonstretchable so that they are enabled to apply a positive differential force couple to the femur and tibia proximal the knee joint.

Each of the posterior thigh strap 28 and anterior pretibial strap 34 has a short length of Velcro hook material 40 on both sides proximate one end, the remainder of both sides being covered with Velcro pad material 42. With this construction, the posterior thigh strap 28 is engaged to the brace 10 from its location shown in FIG. 1 by first lacing the end having the Velcro hook material 40 through the eyelet 30 of lateral femoral side bar 20, then pulling this laced end of strap 28 posteriorly around the back of the thigh, then lacing this same end through the eyelet 30 of medial side bar 20a and doubling the laced end back over the laced strap 28 and anchoring the inner Velcro hook strip 40 to the outer Velcro pad 42, and finally folding the remainder of the strap 28 over such doubled-back end portion and engaging the inner Velcro pad 42 with the exposed outer Velcro hook strip 40 to secure the strap 28. In like manner, the anterior pretibial strap 34 is connected to brace 10 from the location illustrated in FIG. 1 by first lacing its end with Velcro hook material 40 throuqh eyelet 36 of medial side bar 22a, pulling that end portion of strap 42 anteriorly over the tibia, then lacing it through the eyelet 36 on lateral tibial side bar 22 and doubling the hook strip end portion 40 back anteriorly over the exposed side of strap 34, and then doubling the remainder of the strap 34 from the eyelet 36 on medial side bar 22a over the exposed front of the already laced portion of strap 34 and engaging the Velcro pad material 42 with the Velcro hook strip 40 to secure the strap.

The brace 10 is applied to the leg, which already has tubular undersleeve 12 pulled onto it, by stepping through the open center of brace 10 from behind the anterior thigh cuff 24 and then pulling the brace 10 upwardly on the leg until the biaxial hinges 18 are located adjacent the knee joint. The posterior thigh strap 28 and anterior pretibial strap 34 may be connected to the brace 10 after the brace 10 has thus been located on the leg, or alternatively may be prelaced onto the brace 10 in loosened condition, and then cinched up to the desired operative tightness. In practice, it has been found is preferable to tighten each of the straps 28 and 34 as tightly as possible without substantial discomfort so as to bias the tibia rearwardly relative to the femur proximate the knee joint with a positive counterforce on the tibia such as will not only resist anterior translocation of the tibia relative to the femur but will actually counteract such anterior translocation and put a positive posterior traction on the tibia relative to the femur. Such positive traction preloads and compresses the tissues in the knee joint to a maximum extent such that any tendency for the tibia to translocate forwardly relative to the femur is far less than for any knee brace which is adapted to simply block such movement.

Before the posterior thigh strap 28 is tightened against the back of the thigh, it is preferred to place a posterior thigh pad 44 between the strap 28 and the thigh, the pad 44 being made of a foam elastomer such as Neoprene and being secured in position by engagement of a Velcro hook patch 46 thereon with the Velcro pad material 42 on strap 28. Similarly, it is preferred to place an anterior tibial pad 48 between the anterior pretibial strap 34 and the shin for improved comfort of the wearer, the pad 48 being secured in position by engagement of a Velcro hook patch 50 thereon with Velcro pad material 42 on strap 34.

Lateral and medial condyle pads 52 and 54 are mounted directly on hinge plates of the respective lateral and medial hinges 18 as described in detail below, and engage against opposite sides of the knee to control lateral knee instability.

The brace 10 attaches with the undersleeve 12 so as to prevent the brace 10 from migrating downwardly on the leg, and the undersleeve 12 also serves to increase patient comfort while wearing the brace 10. Undersleeve 12 is made of thin (preferably approximately 1/16 inch) foam elastomer sheet material, such as foam Neoprene, preferably with a knit or loop-type fabric bonded to the outer surface thereof. Undersleeve 12 is preferably somewhat longer from its upper end to its lower end 58 than the length of brace 10 to assure that the undersleeve 12 will always remain at least coextensive with the brace 10 during athletic operation of the brace 10. Undersleeve 12 has a patellar aperture 60 therein for knee-cap comfort and as an indicator of correct longitudinal location of the undersleeve 12 on the leg.

Applicants have found in practice that the tubular undersleeve 12 has substantially no tendency to migrate downwardly on the leg because of its continuous conformation with the varying curvatures of the leg from middle thigh to lower calf, and particularly because of the downwardly increasing girth of the calf below the knee. Advantage is taken of such longitudinal stability of the tubular undersleeve 12 against downward migration by positively securing the knee brace 10 to the tubular undersleeve 12 by Velcro means at three discrete longitudinally spaced locations along the length of brace 10. Thus, a pair of anteriorly facing, circumferentially spaced Velcro pad patches 62 on sleeve 12 connect to a corresponding pair of Velcro hook patches 64 within the anterior thigh cuff 24; a pair of lateral and medial Velcro pad patches on sleeve 12 proximate the knee attach to the Velcro hook surfacing of the registering pair of condyle pads 52 and 54; and a pair of posteriorly facing Velcro hook patches 66 on sleeve 12 connect to a registering pair of anterior facing Velcro pad patches 68 in posterior calf cuff 26.

An additional measure is preferably employed to further assure against downward migration of the brace 10, in the form of a pair of thin elastomer overwrap straps, preferably of gum rubber, which wrap around the thigh and calf and attach to the anterior thigh cuff 24 and posterior calf cuff 26, respectively, by Velcro means. Thigh cuff overwrap 72 has a Velcro pad strip 74 on the underside at one end which attaches to a Velcro hook patch 76 on the outside of thigh cuff 24. From the connection of these Velcro units 74 and 76 the thigh overwrap is wrapped all of the way around the thigh until a Velcro hook strip 78 on the underside of its other end is attached to a Velcro pad 80 on the outside of overwrap 72. Similarly, calf cuff overwrap 82 has a Velcro pad strip 84 at one end that is attached to a Velcro hook patch 86 on the outside of cuff 26, the overwrap 82 being wrapped around the calf, with a Velcro hook strip 88 on its underside at the other end attaching to a Velcro pad 90 on the outside of overwrap 82. These cooperative engagements of the thigh and calf overwraps 72 and 82 over the respective thigh and calf cuffs 24 and 26 are illustrated in FIGS. 7–9. The thigh and calf overwraps 72 and 82 secure the open-cuffed ends of the brace 10 to the thigh and calf, respectively, so that extension stop gears in the hinges, described hereinafter in connection with FIGS. 3, 4 and 6 of the drawings, are enabled to prevent hyperextension of the knee, blocking extension at a preferred preset $7\frac{1}{2}°$.

Preferably, all of the four side bars 20, 20a, 22, and 22a are covered with foam elastomer padding sleeves 92, which may be of foam Neoprene and are preferably covered in the same manner as undersleeve 12 with a knit or loop-type fabric.

Figure 10:
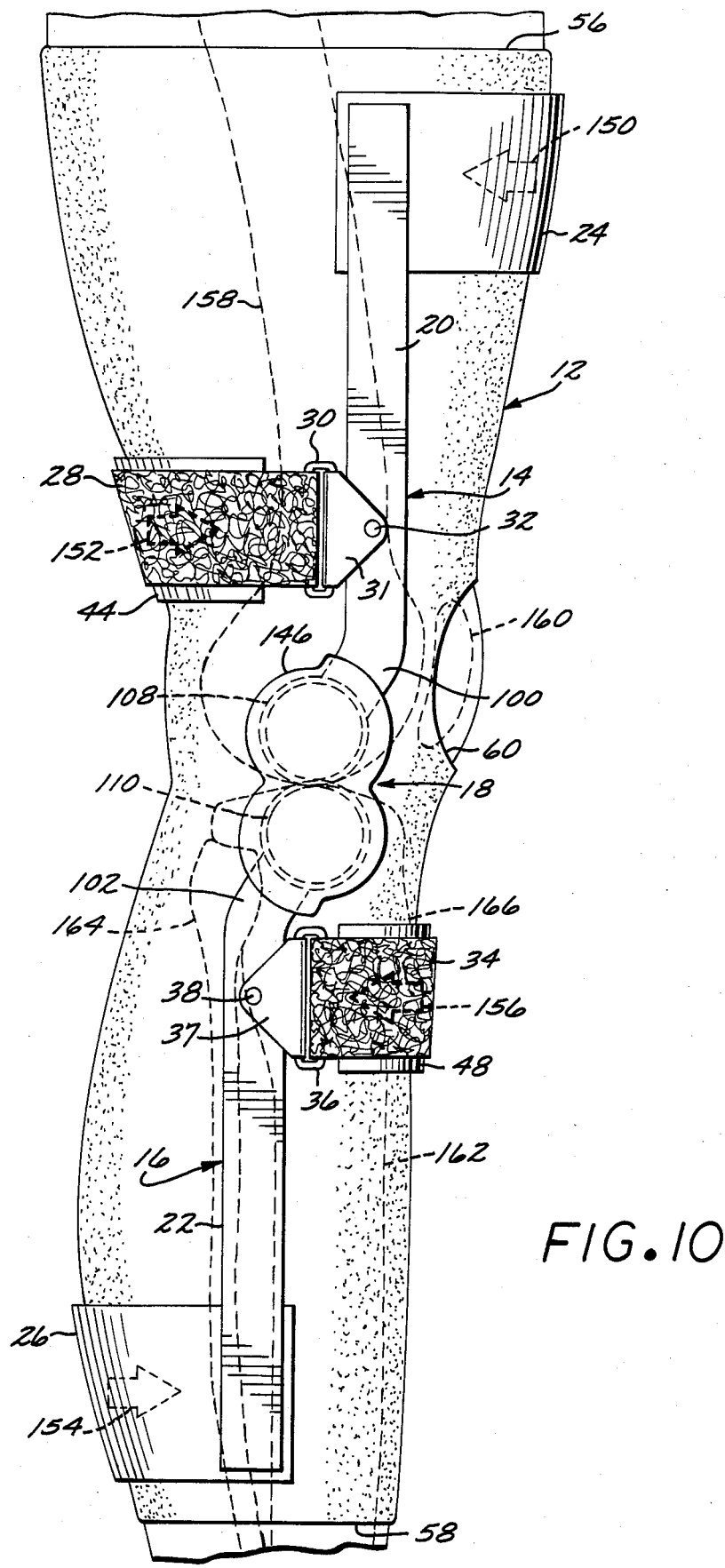
FIG. 10 is a side elevational view looking toward the lateral side of the brace, illustrating the brace and undersleeve of the invention mounted on a leg in an extended condition, showing bones of the leg in dashed lines, and showing the forces of the four-point leverage system of the invention by means of phantom arrows.

As best seen in FIGS. 2, 3 and 10, the femoral side bars 20 and 20a have short posteriorly angled lower end portions designated 100 and 100a, respectively. Conversely, the tibial side bars 22 and 22a have short anteriorly angled upper end portions 102 and 102a, respectively. Otherwise, the principal portions of the lengths of both of the femoral side bars 20 and 20a above the posterior angled lower portions 100 and 100a are preferably straight; and the principal portions of the lengths of both of the tibial side bars 22 and 22a below the anterior angled short upper end portions 102 and 102a are preferably straight. The preferred angle of inclination of each of the lower end portions 100 and 100a relative to the principal straight portion of its respective femoral side bar 20 and 20a is approximately 45°. Similarly, the preferred angle of inclination of the upper end portions 102 and 102a relative to the principal straight portions of tibial side bars 22 and 22a is approximately 45°.

The short angled end portions 100, 100a, 102, and 102a of the side bars located proximal the hinge structures 18 are for the purpose of placing the principal, straight lengths of the femoral side bars 20 and 20a anteriorly along the sides of the thigh, while at the same time placing the principal, straight lengths of the tibial side bars 22 and 22a posteriorly along the sides of the calf. This then enables the posterior thigh strap 28 to have at least approximately 180° of strap loop arc around the back of the thigh for maximum mechanical advantage of the femur lever 14; while at the same time enabling the anterior pretibial strap 34 to also have at least approximately 180° of strap loop arc around the front of the shin proximal the tibial tubrical to assure maximum mechanical advantage of the tibia lever 16.

Viewing the brace 10 from the front as in FIGS. 1 and 7, it will be seen that the medial tibial side bar 22a has a lateral offset, designated 103, between the hinge structure 18 and strap mounting eyelet 36. This is to accommodate the natural lateral offset of the shin below the knee joint.

It is desirable that the hinge joints 18 between the anteriorly offset femoral side bars 20 and 20a and the respective posteriorly offset tibial side bars 22 and 22a be bicentric or biaxial, and if so, it is essential that they be geared. Because of the complex bending action of the knee joint, a single pivot is generally incompatible with the movement of the knee joint and would unduly stress the knee under the loading necessarily imposed by the brace 10 of the invention. A biaxial or bicentric hinge of correct dimensions is, on the other hand, substantially completely compatible in its action with the action of the knee joint, and therefore does not undesirably stress the knee under the loading of the brace 10 of the invention.

A reason for the essentiality of the geared connections in the hinges 18 if they are bicentric is that for operability of the present invention in applying rearward traction to the tibia relative to the femur proximal the knee joint, there can be no relaxing of the tension of either the posterior thigh strap 28 or the anterior pretibial strap 34 that might originate at the hinge structures 18. Thus, with bicentric hinges that were not geared, the hinges could rock or tilt, which would be in a counter-clockwise direction as viewed in FIGS. 2 and 8-10, which would then cause relaxation of both the posterior thigh strap 28 and the anterior pretibial strap 34, thereby defeating the operability of both the femur lever 14 and the tibia lever 16. However, the geared connection between the hinged ends of femoral side bars 20 and 20a and respective tibial side bars 22 and 22a positively interlocks the hinged ends of the tibial side bars 22 and 22a against anterior shifting relative to the respective hinged ends of the femoral side bars 20 and 20a, thereby providing positive assurance against such relaxation at the hinges 18.

Not only do the geared connections in the hinges 18 positively prevent such relaxation, but as a further aspect of this bicentric, geared connection, during flexion from the straight, extended position of the knee joint shown in FIG. 10 to a flexed position such as shown in FIG. 8, the gears affixed to the upper ends of the tibial side bars 22 and 22a in effect climb or roll rearwardly along the peripheries of the mating gears affixed to the lower ends of the femoral side bars 20 and 20a, respectively, serving to add further traction of the anterior pretibial strap 34 relative to the posterior thigh strap 28, thereby pulling the tibia anteriorly relative to the femur even further during flexion.

In addition to these reasons for the geared bicentric or biaxial hinges 18, the geared connection in hinges 18 maintains the anterior offset of femoral side bars 20 and 20a and the posterior offset of tibial side bars 22 and 22a, and thereby maintains the full approximately 180° of strap loop arcs to assure maximum mechanical advantage for each of the femur and tibia levers 14 and 16, and hence for the entire four-point leverage system of the brace 10. The preferred amount of anterior/posterior offset of the principal straight portions of femoral side bars 20 and 20a relative to the principal straight portions of tibial side bars 22 and 22a in the extended, parallel relationship as illustrated in FIGS. 2 and 10 is approximately two inches, and the preferred minimum offset is approximately one and one-half inches. It is also preferred that the femoral and tibial side bar offsets from the centers of hinges 18 be substantially equal and opposite in the anterior and posterior directions, respectively.

The hinges 18 are the same on the lateral and medial sides of the brace 10, so only one of these hinges, the lateral hinge 18, has been shown in detail in the drawings, in FIGS. 3-6. For stability in supporting the hinge gears on the angled ends of the side bars, the angled ends 104 of femoral side bars 20 and 20a and the angled ends 106 of tibial side bars 22 and 22a are enlarged in area. An arcuate gear 108 is rigidly affixed to the lateral side of each enlarged end 104, and an arcuate gear 110 is rigidly affixed to the lateral side of each of the enlarged ends 106. Each of the femoral bar gears 108 is in meshing engagement with the respective one of the tibial bar gears 110.

Each hinge 18 has a pair of elongated, flat, parallel hinge plates generally longitudinally arranged relative to the brace 10, including an inner hinge plate 112 which lies medially of the side bar ends 104 and 106, and an outer hinge plate 114 which lies laterally of the gears 108 and 110. A pair of hinge pins 116 and 118, preferably rivets as illustrated, extend through both hinge plates 112 and 114 near their longitudinal ends and extend through the arcuate centers of respective gears 108 and 110 and respective enlarged side bar ends 104 and 106. Suitable antifriction washers such as the washers 120 may be carried on the hinge pins 116 and 118 to maximize freedom of movement in the hinge structure 18. A support 122 for condyle pad 52 is attached to the center of inner hinge plate 112 by means of a screw 124.

An extension stop gear 126, in the form of a small spur gear, is carried on an arm 128 located between hinge gear 108 and plate 114, the arm 128 being hinged on pin 116. Stop gear 126 is mounted on arm 128 by means of a screw 130. The extension stop gear 126 meshes with the arcuate gear rack of hinge gear 108. Screw 130 holds stop gear 126 in frictional engagement with the arm 128, screw 130 being staked to gear 126 so that stop gear 126 can be rotated by screw 130 for adjustable positioning along the periphery of hinge gear 108. A pointer 132 on arm 128 indicates the limit of extension of the brace 10, and hence correspondingly of the knee joint, that will be permitted by any particular positioning of stop gear 126 on hinge gear 108. FIG. 6 illustrates the brace 10 in a position of approximately 90° of flexion, and it will be seen that in such position the extension stop gear 126 is moved with its hinge gear 108 counterclockwise approximately 90° from engagement with the other hinge gear 110. Then, as flexion decreases, stop gear 126 as carried by hinge gear 108 moves clockwise toward the other hinge gear 110 until it finally engages against the gear 110 as a wedge between the two gears 108 and 110 as seen in FIG. 3 to positively stop further extension of the brace.

Similarly, a flexion stop gear 136 is adjustably carried on the tibial hinge gear 110, being rotatably adjustably mounted by a screw 140 on an arm 138 that is pivoted on pin 118. As seen in FIG. 5, the screw 140 holds flexion stop gear 136 in frictional engagement against the arm 138 and is staked to flexion stop gear 136 so that stop gear 136 can be adjustably positioned along the arcuate rack of hinge gear 110 by adjustment of screw 140 to the desired limit of flexion to be permitted. Such flexion limit is indicated by means of a pointer 142 on arm 138 which points to flexion index 144 on gear 110.

Each of the hinges 118 is covered by a hinge cover shell 146 attached to outer hinge plate 114 by means of a screw 148. The hinge cover shells 146 are removed for access to the extension and flexion stop gear mechanisms for adjustment of the latter. The pair of extension stop gears 126 and flexion stop gears 136 on opposite sides of brace 10 will be set to the same amount of extension on the one hand and flexion on the other hand.

Referring now to FIG. 10, the forces involved in the four-point lever system of the present invention are illustrated by phantom arrows on the four members which are applying forces to the leg. Thus, in the femur lever 14, a posterior force 150 is applied by the fulcrum cuff 24 against the front of the thigh distally of the knee joint; while the posterior thigh strap 28 applies an anterior force 152 against the rear of the thigh proximally of the knee joint. Conversely, in the tibia lever 16, the fulcrum cuff 26 applies an anterior force 154 against the rear of the calf distally of the knee joint; while the anterior pretibial strap 34 applies a posterior force 156 against the front of the shin proximally of the knee joint. Because of the geared interlock between the angled ends of the femoral side bars 20 and 20a and the angled ends of the respective tibial side bars 22 and 22a, a force couple is developed between the two forces 152 and 156 proximal the knee joint to serve the very same function as the anterior cruciate ligament within the knee, namely, to resist anterior drawer shift of the tibia relative to the femur proximal the knee joint.

FIG. 10 provides a good illustration of the structural compatibility between the brace 10 of the present invention and the bone structure within the knee. Thus, most of the lengths of the femoral side bars 20 and 20a laterally and medially overlap the femur 158; most of the lengths of the tibial side bars 22 and 22a overlap the lateral and medial sides of the tibia 162 and fibula 164; and the angled end portions 100 and 100a of the femoral side bars and 102 and 102a of the tibial side bars overlap the lateral and medial sides of the enlarged ends of the femur 158, tibia 162 and fibula 164 proximal the knee joint. FIG. 10 also illustrates the freedom allowed the knee in the region of patella 160 by the patellar aperture 60 in undersleeve 12.

One of the surprising things which distinguishes the present invention from all prior art knee orthotics of which applicants are aware is the fact that none of the four principal elements of the brace which cooperate to externally reproduce the function of the anterior cruciate ligament extends all of the way around the leg. This is important for a number of reasons. First, and of primary importance, the two straps 28 and 34 which apply the torquing force couple to the femur and tibia proximal the knee are not either one reduced in force-applying capacity by an opposing loop at the same longitudinal location extending around the other side of the leg. Thus, the posterior thigh strap 28 has its full force effectively applied anteriorly to the femur proximal the knee joint, without opposition from any strap or other loop extending anteriorly around the thigh at the same longitudinal location, which would otherwise pull against the leverage gained by the posterior thigh strap 28. Similarly, the anterior pretibial strap 34 is unopposed by any strap or other structure extending posteriorly around the calf at the same longitudinal location that would otherwise pull against the leverage gained by the anterior pretibial strap 34.

Another important advantage of the simple half-loop concept of the present invention embodied in all four of the leg-engaging lever structures, including the cuffs 24 and 26 and the straps 28 and 34, is that this arrangement substantially eliminates projecting structures like those of the prior art which would interfere with athletic performance and thereby render the apparatus virtually useless for athletic use.

Applicants' cuff overwraps 72 and 82 serve no function in the four-point leverage operation of applicants' brace 10 as a substitute or replacement for an injured anterior cruciate ligament, and need not be applied so tightly as to in any way interfere with blood circulation in the leg. To the contrary, most prior art knee orthotics of which applicants are aware rely upon bands of one sort or another which completely encircle the leg both above and below the knee, and which depend for their utility upon their tightness so as to tend to interfere with blood circulation in the leg and to be uncomfortable in use.

Applicants' use of only half-loop type structures in the four leverage units, the two cuffs 24 and 26 and the two straps 28 and 34, further enables applicants' brace 10 to have a minimum of weight and bulk that would otherwise interfere with athletic performance.

While applicants' knee brace 10 is primarily for the purpose of limiting anterior drawer shift of the proximal tibia, while serving this function it also synergistically controls rototory instability movements which might occur with injury of some of the secondary restraining structures in the knee. This is because rototory instability movements generally require some forward translocation of the tibia relative to the femur which relieves interengagement between the intercondular eminence on the tibial plateau and a matching irregularity of the femur. However, with the control the present invention applies against forward translocation of the tibia relative to the femur, the intercondular eminence and matching femur irregularity are maintained in close interfitting relationship against rototory motion.

Applicants have conducted clinical anterior drawer tests on 79 patients with a torn anterior cruciate ligament in one leg. Normally, in a healthy person without anterior drawer trauma in either knee, the anterior drawer will be approximately the same for both knees under the application of various anterior drawer forces. However, if the anterior cruciate ligament in one knee is torn, then under any applied translocating force the injured knee will translocate a considerably larger amount than the healthy knee. Thus, to test the effectiveness of the brace 10 of the invention as a replacement or substitute for an injured anterior cruciate ligament, on each of the 79 persons tested applicants tested the uninjured knee, the injured knee without the present invention, and the injured knee with the present invention. These three comparative tests were run for three separate anterior drawer applied forces, a measured 15 lbs., a measured 20 lbs., and an estimated 60 lbs. The results of these tests established not only that the present invention was effective in completely replacing or substituting for the injured anterior cruciate ligament, but on the average the present invention controlled tibial anterior drawer movement in the injured knee better than the real anterior cruciate ligament controlled it in the good knee. Thus, at 15 lbs. applied force, 90 percent of the injured knees tested as good or better than the noninvolved knee; at 20 lbs. applied force, 74 percent tested as good or better than the noninvolved knee; and at an estimated 60 lbs. applied force, 75 percent tested as good or better than the noninvolved knee. There was greater than 50 percent reduction in anterior drawer shift with the present invention applied in every knee tested, and in some cases there was as much as 80 percent reduction in the amount of anterior drawer shift.

The averages and ranges for all knees tested were as follows. At 15 lbs. applied force, the good knees averaged approximately 5 mm of anterior excursion, and ranged from approximately 1 mm to approximately 10 mm; the injured knees without the present invention averaged approximately 10 mm and ranged from approximately 4 mm to approximately 17 mm; while with the present invention applied, they averaged only 3 mm and ranged from approximately 1 mm to approximately 7 mm. With 20 lbs. force applied, the good knees averaged an anterior excursion of approximately 7 mm, with a range of from approximately $1\frac{1}{2}$ mm to approximately $11\frac{1}{2}$ mm; the injured knees averaged approximately $12\frac{1}{4}$ mm, and ranged from approximately $4\frac{1}{2}$ mm to approximately 20 mm; while with the present invention applied, the injured knees averaged approximately $4\frac{3}{4}$ mm, and ranged from approximately $2\frac{1}{2}$ mm to approximately $9\frac{1}{2}$ mm. With approximately 60 lbs. of applied force, the good knees averaged approximately 8 mm of anterior excursion, and ranged from approximately $2\frac{1}{2}$ mm to approximately 12 mm; the injured knees averaged approximately 15 mm, and ranged from approximately $5\frac{1}{2}$ mm to approximately 20 mm; while with the present invention applied, they averaged approximately $6\frac{1}{3}$ mm, and ranged from approximately $2\frac{1}{2}$ mm to approximately 11 mm.

While the instant invention has been described with regard to a particular embodiment, modifications may readily be made by those skilled in the art, and it is intended that the claims cover any such modifications which fall within the spirit and scope of the invention.

We claim:

1. A knee brace for applying a net differential force couple to the femur and tibia of the knee to serve the function of an anterior cruciate ligament, which comprises:
   (a) a femur lever oriented generally longitudinally of the thigh, comprising
      (1) a femur connecting element,
      (2) an anterior thigh fulcrum means on an upper portion of said femur lever attached to said femur connecting element for applying a net posteriorly directed force component against the front of the thigh distally of the knee joint, and
      (3) posterior thigh-engaging means on a lower portion of said femur lever attached to said femur connecting element for applying a net posteriorly directed force component against the back of the thigh proximal the knee joint,
   (b) a tibia lever oriented generally longitudinally of the calf, comprising
      (1) a tibia connecting element,
      (2) a posterior calf fulcrum means on a lower portion of said tibia lever attached to said tibia connecting element for applying a net anteriorly directed force component against the back of the calf distally of the knee joint, and
      (3) anterior shin-engaging means on an upper portion of said tibia lever attached to said tibia connecting element for applying a net posteriorly directed force component against the front of the shin proximal the knee joint; and
   (c) hinge means hingedly connecting the lower end of said femur lever and the upper end of said tibia lever,
      said femur lever and said tibial lever applying, in use, a net differential force couple having an anteriorly directed force component to the femur and a posteriorly directed force component to the tibia proximal the knee joint so as to externally serve the function of the anterior cruciate ligament.

2. A knee brace as defined in claim 1, wherein said posterior thigh-engaging means and said anterior shin-engaging means each comprise open, adjustably tightenable, substantially nonstretchable strap means.

3. A knee brace as defined in claim 2, wherein said anterior thigh fulcrum means and said posterior calf fulcrum means each comprise open, generally arcuate cuff means.

4. A knee brace as defined in claim 3, wherein said anterior thigh cuff means is substantially rigid.

5. A knee brace as defined in claim 4, wherein said anterior thigh cuff means is formably adjustable.

6. A knee brace as defined in claim 3, wherein said posterior calf cuff means is flexible but substantially nonstretchable.

7. A knee brace as defined in claim 3, wherein said anterior thigh cuff means is substantially rigid, and said posterior calf cuff means is flexible but substantially nonstretchable.

8. A knee brace as defined in claim 1 which further comprises a tubular, elastomeric undersleeve adapted to be elastically engaged over the knee and adjacent portions of the thigh and calf of a leg upon which said knee brace is to be worn; and
   fastening means releasably connectable between said brace and said undersleeve whereby said undersleeve resists downward migration of said brace on the leg.

9. A knee brace as defined in claim 8, wherein said fastening means comprises Velcro.

10. A knee brace as defined in claim 9, wherein said fastening means comprises attachments at each of said thigh and calf fulcrum means.

11. A knee brace as defined in claim 3 which further comprises elastomeric overwrap strap means adapted to be engaged around the thigh and calf so as to overlie the repsective said thigh and calf cuff means.

12. A knee brace as defined in claim 1, wherein said femur lever comprises a pair of femoral connecting elements adapted to be located on opposite sides of the thigh, and said tibial lever comprises a pair of tibial connecting elements adapted to be located on opposite sides of the calf, said hinge means comprising a pair of hinges hingedly connecting the femoral and tibial connecting elements on opposite sides of the brace so as to positively interlock the hinged end of said tibia lever against anterior shifting relative to the hinged end of said femur lever.

13. A knee brace as defined in claim 12, wherein said posterior thigh-engaging means and said anterior shin-engaging means each comprise adjustably tightenable, substantially nonstretchable strap means connected between the respective said femoral and tibial connecting elements.

14. A knee brace as defined in claim 13, wherein said anterior thigh fulcrum means and posterior calf fulcrum means each comprise open, generally arcuate cuff means connected between the respective femoral and tibial connecting elements.

15. A knee brace as defined in claim 13, wherein said femoral connecting element proximate said posterior thigh-engaging strap means are displaced forwardly of said hinges so as to enable said posterior thigh-engaging strap means to have approximately 180° of engagement around the back of the thigh.

16. A knee brace as defined in claim 13, wherein said tibial connecting elements proximate said anterior shin-engaging strap means are displaced rearwardly of said hinges so as to enable said anterior shin-engaging strap means to have approximately 180° of engagement around the front of the shin.

17. A knee brace as defined in claim 13, wherein said femoral connecting elements proximate said posterior thigh-engaging strap means are displaced forwardly of said hinges, and said tibial connecting elements proximate said anterior shin-engaging strap means are displaced rearwardly of said hinges, whereby each of said strap means is enabled to have approximately 180° of engagement around the leg.

18. A knee brace as defined in claim 17, wherein said femoral and tibial connecting element displacements are substantially equal.

19. A knee brace as defined in claim 18, wherein the total front/rear displacement between said femoral and tibial connecting elements is at least approximately 1½ inches.

20. A knee brace as defined in claim 18, wherein the total front/rear displacement between said femoral and tibial connecting elements is approximately 2 inches.

21. A knee brace as defined in claim 17, wherein the principal portions of the lengths of said femoral and tibial connecting elements are generally straight, and said displacements are accomplished by rearwardly and downwardly angled portions of said femoral connecting elements adjacent said hinges and forwardly and upwardly angled portions of said tibial connecting elements adjacent said hinges.

22. A knee brace as defined in claim 21, wherein said angled portions of said connecting elements are angled at approximately 45° relative to said generally straight portions.

23. A knee brace as defined in claim 12 which further comprises a pair of opposed, elastomeric condyle pads mounted on the respective said hinges.

24. A knee brace as defined in claim 12, wherein each of said hinges comprises a bicentric hinge, the hinged ends of said femoral and tibial connecting elements being gear-connected at the hinges on opposite sides of the brace.

25. A knee brace as defined in claim 24, wherein each of said hinges further comprises a pair of adjustable spur stop gears for adjustably limiting the amount of extension and flexion of the brace.

* * * * *

UNITED STATES PATENT AND TRADEMARK OFFICE
CERTIFICATE OF CORRECTION

PATENT NO. : 4,697,583

DATED : OCTOBER 6, 1987

INVENTOR(S) : MASON et al.

It is certified that error appears in the above-identified patent and that said Letters Patent is hereby corrected as shown below:

Column 14, line 2, "posteriorly" should read -- anteriorly --.

Signed and Sealed this

Third Day of May, 1988

Attest:

DONALD J. QUIGG

Attesting Officer

Commissioner of Patents and Trademarks